(12) United States Patent
Korber et al.

(10) Patent No.: US 11,182,392 B2
(45) Date of Patent: Nov. 23, 2021

(54) SYSTEM AND METHODS THEREOF FOR GENERATION OF AN AIR QUALITY SCORE

(71) Applicant: Breezometer Ltd., Haifa (IL)

(72) Inventors: Ran Korber, Yokneam Illite (IL); Ziv Lautman, San Francisco, CA (US); Emil Fisher, Kiryat Ata (IL)

(73) Assignee: BREEZOMETER LTD., Haifa (IL)

( * ) Notice: Subject to any disclaimer, the term of this patent is extended or adjusted under 35 U.S.C. 154(b) by 402 days.

(21) Appl. No.: 15/289,683

(22) Filed: Oct. 10, 2016

(65) Prior Publication Data

US 2017/0038088 A1 Feb. 9, 2017

Related U.S. Application Data

(63) Continuation of application No. PCT/US2015/029625, filed on May 7, 2015.
(Continued)

(51) Int. Cl.
*G06F 16/2457* (2019.01)
*F24F 3/16* (2021.01)
(Continued)

(52) U.S. Cl.
CPC ......... *G06F 16/24578* (2019.01); *F24F 3/16* (2013.01); *F24F 11/30* (2018.01); *F24F 11/62* (2018.01); *G01N 33/0036* (2013.01); *F24F 8/99* (2021.01); *F24F 11/52* (2018.01); *F24F 11/58* (2018.01); *F24F 11/63* (2018.01); *F24F 2110/50* (2018.01); *F24F 2110/52* (2018.01)

(58) Field of Classification Search
CPC ........ F24F 11/0017; F24F 3/16; F24F 11/006; G06F 16/24578
See application file for complete search history.

(56) References Cited

U.S. PATENT DOCUMENTS 6,782,351 B2 * 8/2004 Reichel ............. G01N 33/0075
340/501
6,975,975 B2 * 12/2005 Fasca .................... G05B 17/02
110/345
(Continued)

FOREIGN PATENT DOCUMENTS

KR 20100130735 A 12/2010

OTHER PUBLICATIONS

The International Search Report and the Written Opinion for PCT/US2015/029625, ISA/RU Moscow, Russia, dated Aug. 27, 2015.

*Primary Examiner* — Christine A Enad
(74) *Attorney, Agent, or Firm* — The Law Office of Joseph L. Felber

(57) ABSTRACT

A system and method for generating air quality scores for air quality within certain locations are presented. The method includes identifying at least one air pollution source within the predetermined perimeter around the at least one location; extracting an air quality score range based on the at least one location from at least one data source; identifying at least one environmental variable based on the at least one location and the at least one time parameter; simulating at least one air pollution measurement based on the at least one environmental variable and the at least one air pollution source; and generating at least one air quality score respective of the air quality score range, wherein the at least one air quality score is based on the at least one air pollution measurement.

23 Claims, 3 Drawing Sheets

Related U.S. Application Data

(60) Provisional application No. 61/991,552, filed on May 11, 2014.

(51) Int. Cl.

| | | |
|---|---|---|
| *F24F 11/30* | (2018.01) | |
| *F24F 11/62* | (2018.01) | |
| *G01N 33/00* | (2006.01) | |
| *F24F 110/50* | (2018.01) | |
| *F24F 110/52* | (2018.01) | |
| *F24F 11/63* | (2018.01) | |
| *F24F 11/58* | (2018.01) | |
| *F24F 11/52* | (2018.01) | |
| *F24F 8/99* | (2021.01) | |

(56) References Cited

U.S. PATENT DOCUMENTS

| | | | |
|---|---|---|---|
| 3,560,146 | A1 | 10/2013 | Kwon et al. |
| 8,744,766 | B2* | 6/2014 | Rakshit .............. G01C 21/3469 340/632 |
| 2007/0112511 | A1* | 5/2007 | Burfeind ........... G06F 17/30241 701/469 |
| 2009/0094047 | A1* | 4/2009 | Hyde ..................... G06Q 40/08 705/1.1 |
| 2009/0273470 | A1 | 11/2009 | Sinkevicius et al. |
| 2011/0009986 | A1* | 1/2011 | Page .................. G01N 33/0031 700/90 |
| 2012/0092649 | A1* | 4/2012 | Wong ...................... G01W 1/00 356/72 |
| 2013/0174646 | A1* | 7/2013 | Martin ................... G01N 33/00 73/31.02 |
| 2013/0179078 | A1* | 7/2013 | Griffon .................. G06Q 50/26 702/3 |
| 2014/0039988 | A1* | 2/2014 | Londergan ......... G06Q 30/0207 705/14.1 |
| 2015/0117767 | A1* | 4/2015 | Gong ....................... G06K 9/00 382/160 |
| 2015/0217057 | A1* | 8/2015 | Hogdahl ............. A61M 5/2033 604/117 |

* cited by examiner

SYSTEM AND METHODS THEREOF FOR GENERATION OF AN AIR QUALITY SCORE

CROSS REFERENCE TO RELATED APPLICATIONS

This application is a continuation of PCT application No. PCT/US2015/029625, filed on May 7, 2015 which claims the benefit of U.S. Provisional Patent Application No. 61/991,552 filed on May 11, 2014, the contents of which are hereby incorporated by reference.

TECHNICAL FIELD

The disclosure generally relates to environmental protection systems and more specifically to systems and methods for measuring air quality within certain locations.

DESCRIPTION OF THE BACKGROUND

Air pollutants are substances in the air that can have negative effects on humans. The substances can be solid particles, liquid droplets, gases, and so on. An air pollutant can be of natural origin or man-made.

Although air pollution is a well-known phenomenon worldwide, the problem is that people are usually unaware that the air they breathe may harm them. Ironically, there are many cases where people can immediately improve the air quality in their close environment by simple actions.

Different types of air pollution monitoring systems collect different variables using different techniques. Due to the complexity of the architecture of each air pollution monitoring system it is difficult to aggregate the different data items received from different of air pollution monitoring systems.

It would be therefore advantageous to provide a solution that overcomes the limitations of the prior art by determining air quality within certain areas. It would further be advantages if such a solution was capable of providing recommendations on how to minimize an exposure to pollutants.

BRIEF DESCRIPTION OF THE DRAWINGS

The subject matter disclosed herein is particularly pointed out and distinctly claimed in the claims at the conclusion of the specification. The foregoing and other objects, features and advantages of the disclosed embodiments will be apparent from the following detailed description taken in conjunction with the accompanying drawings.

SUMMARY

Figure 1:
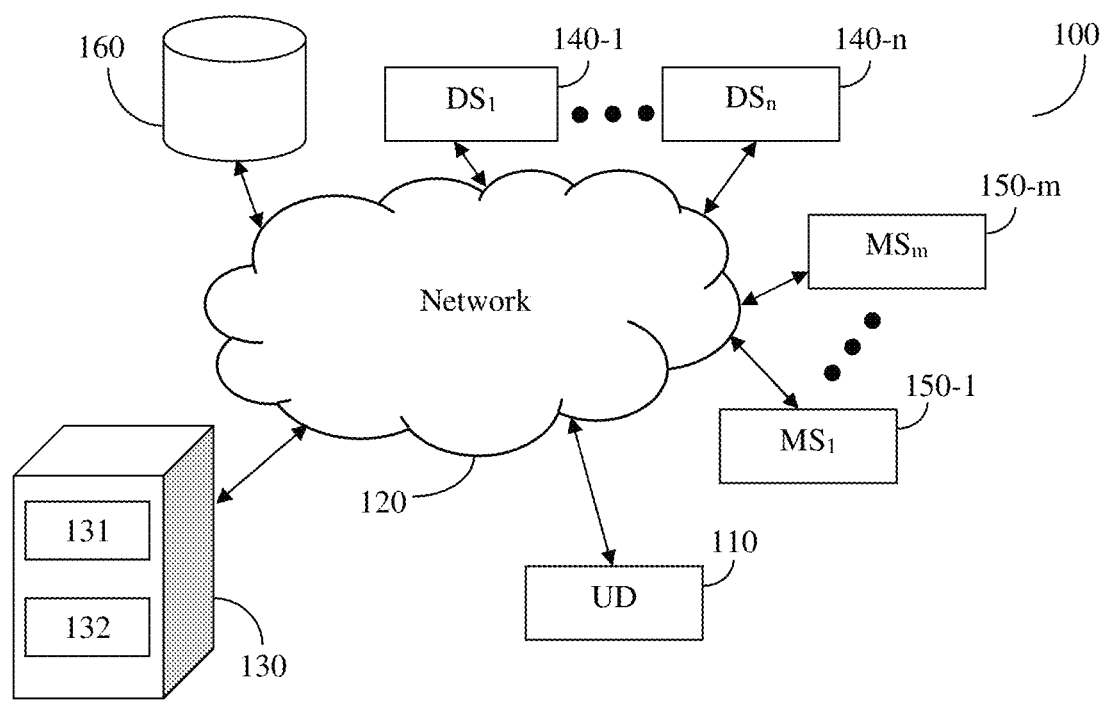
FIG. 1 is a schematic diagram a system utilized to describe the various disclosed embodiments.

Certain embodiments discloses herein include a method for generation of an air quality score. The method comprises identifying at least one air pollution source within the predetermined perimeter around the at least one location; extracting an air quality score range based on the at least one location from at least one data source; identifying at least one environmental variable based on the at least one location and the at least one time parameter; simulating at least one air pollution measurement based on the at least one environmental variable and the at least one air pollution source; and generating at least one air quality score respective of the air quality score range, wherein the at least one air quality score is based on the at least one air pollution measurement.

Certain embodiments disclosed herein also include a system for generating air quality score based on at least one location, a predetermined perimeter, and at least one time parameter, comprising a processor; and a memory, the memory containing instructions that, when executed by the processor, configure the system to identify at least one air pollution source within the predetermined perimeter around the at least one location; extract an air quality score range based on the at least one location from at least one data source; identify at least one environmental variable based on the at least one location and the at least one time parameter; simulate at least one air pollution measurement based on the at least one environmental variable and the at least one air pollution source; and generate at least one air quality score respective of the air quality score range, wherein the at least one air quality score is based on the at least one air pollution measurement.

DETAILED DESCRIPTION

The embodiments disclosed herein are only examples of the many possible advantageous uses and implementations of the innovative teachings presented herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

A system generates air quality scores for air quality at certain locations. The system receives a location and a time parameter. The system is configured to identify air pollution sources within a predetermined perimeter based on the location. The system is further configured to extract an air quality score range based on the perimeter. The system identifies environmental variables based on the location and the time parameter. The system simulates at least one air pollution measurement based on the environmental variables and the pollution sources within the perimeter. The system generates an air quality score respective of the air quality score range based on the air pollution measurement in the location. According to an embodiment, the system is further configured to provide recommendations based on the air quality score. The recommendations include information on how to minimize exposure to air pollution.

FIG. 1 depicts an exemplary and non-limiting schematic diagram of a system 100 utilized to describe various embodiments disclosed herein. A user device 110 is connected to a network 120. The user device 110 may be, but is not limited to, a smart phone, a mobile phone, a laptop, a tablet computer, a personal computer (PC), a wearable computing device, and so on. The network 120 may be, but is not limited to, a local area network (LAN), a wide area network (WAN), a metro area network (MAN), the world wide web (WWW), the Internet, a wired network, a wireless network, and the like, as well as any combination thereof.

The user device 110 is configured to communicate with a server 130 which is also connected to the network 120. The server 130 is configured to receive at least one location from the user device 110 for the purpose of generating an air quality score of the air quality in the at least one location.

The server 130 typically comprises a processing unit 131 that is communicatively connected to a memory 132. The memory contains instructions that can be executed by the processing unit. In an embodiment, the at least one location may be received as coordinates. The coordinates may be, for example, an address, a global positioning system (GPS) signal, and the like. The coordinates may be static (e.g., a certain address) or dynamic (e.g., a certain route through which the user device 110 passes). The server 130 is further configured to receive at least one time parameter from the user device 110. In an embodiment, each time parameter may be a certain time period such as, for example, the month of January 2016.

The server 130 is configured to identify at least one air pollution source within a predetermined perimeter based on the at least one location. The perimeter is determined based on the at least one location where for example, each location may act as the center point for a perimeter. The perimeter may be, for example, a circular area, a triangular area, a square area, etc. The perimeter is defined, in a case of a circular area for example by a radius. According to one embodiment, the server 130 identifies the air pollution sources by fetching locations of known air pollution sources from at least one data source 140-1 through 140-*n* (hereinafter referred to collectively as data sources 140 or individually as a data source 140, merely for simplicity purposes) over the network 120, where n is an integer equal to or greater than 1. The data sources 140 may be, for example, air pollution monitoring systems within the perimeter. The air pollution sources may include, for example, heavy transportation, generating stations (particularly those that burn, for example, fossil fuels such as oil and coal), factories, office buildings, incineration of garbage, and so on.

The server 130 is further configured to extract an air quality score range based on the perimeter. An air quality score range is an index which is usually determined by the authorities in order to assist them in monitoring the air pollution within their territories. Such air quality score ranges are publically available and can be extracted by the server 130 from the one or more data sources 140 over the network 120. The air quality score range may include air pollution scores based on certain air pollution sources within the location. Such air quality score ranges may vary from one location to another. For example, a certain air pollution source may be considered highly pollutant in USA and not pollutant at all in China. Furthermore, the air quality score ranges in different locations may include different indicators as well as different definitions.

The server 130 is further configured to identify at least one environmental variable based on the at least one location and the at least one time parameter. The environmental variables may include, for example, meteorological parameters, topographical data, traffic data, a combination thereof, and so on. The meteorological parameters may be, for example, wind speed and direction, air temperature, air pressure, air humidity, precipitation, haze and contents of the air, solar and terrestrial radiation, and so on. According to one embodiment, the meteorological parameters may be extracted from, for example, at least one meteorological center's servers 150-1 through 150-*m* over the network 120, where m is an integer equal to or greater than 1.

The server 130 is configured to simulate at least one air pollution measurement based on the environmental variables and the at least one air pollution source within the perimeter. The simulation is achieved by the server 130 based on historical cases in proximity to the environmental variables and the at least one air pollution source within the perimeter. Then, the server 130 is configured to generate at least one air quality score respective of the air quality score range based on the at least one air pollution measurement. The air quality score shall be represented as an icon or other marker over a display of the air quality score range. The air quality score represents the air quality level within the perimeter and according to the air quality score range of the location. The at least one air quality score may be sent to the user device 110. Optionally, the server 130 can generates air quality maps. The air quality maps are topographic and/or thermal air pollution maps that show the air quality in certain areas based on the at least one air quality score. Air quality maps are described further herein below with respect to FIG. 3. The air quality map and/or the at least one air quality score may further be sent by the server 130 to display via the network 120 in, for example, a website, a widget, an application program, and so on.

According to one embodiment, the system 100 further includes a database 160 communicatively connected to the server 130 over the network 120. The database 160 is configured to store air quality scores generated by the server 130 for further use. One exemplary use may be to predict future air quality scores of a location based on data existing in the database 160. According to another exemplary embodiment, past air quality scores may be used to provide statistical and other analytics representations of air quality in certain areas.

According to one embodiment, the server 130 is further configured to provide at least one recommendations to the user device 110 based on the at least one air pollution measurement and/or the respective air quality scores. The recommendations include information on how to minimize exposure to air pollution. The recommendations are generated by the server 130 based on the types of air pollution sources within the location. For example, in cases where wind carries air pollution from north of the perimeter, a recommendation may be to prevent protruding of air from northern windows of a structure. According to another embodiment, the recommendations are extracted by the server 130 from the database 160.

According to yet another embodiment, the server 130 is further configured to receive at least one personal variables related to a user of the user device 110 over the network 120. Such personal variables may include, for example: the user's age, parameters related to the user's lifestyle, and so on. Based on the variables, the server 130 is configured to generate personalized recommendations to the user of the device 110. As an example, in case a user commonly takes a route from a first location to a second location, the server 130 is configured to determine the route with a minimum air pollution exposure.

Figure 2:
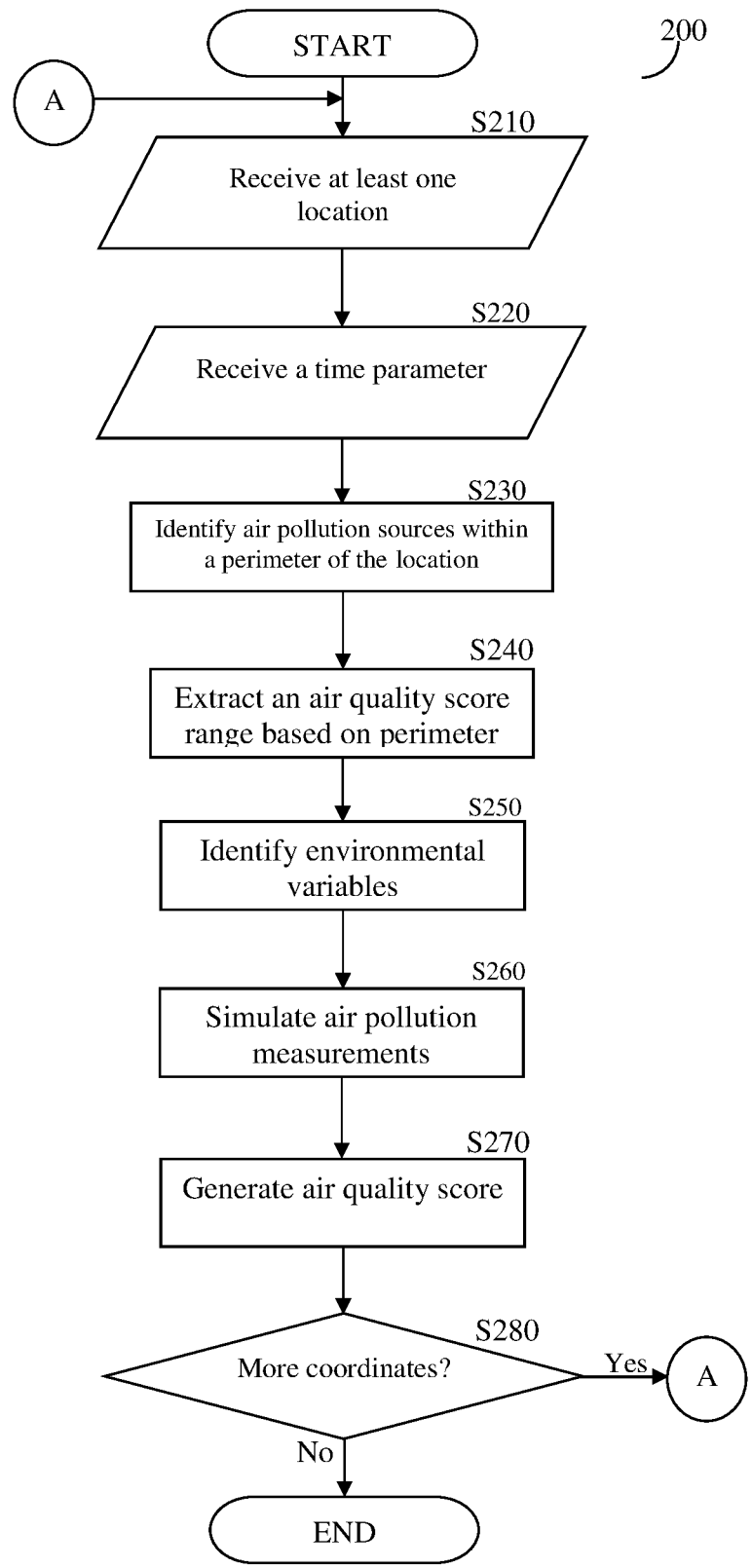
FIG. 2 is a flowchart illustrating a method for generating air quality scores according to an embodiment.

FIG. 2 depicts an exemplary and non-limiting flowchart 200 of a method for generating an air quality score according to one embodiment. In S210, the at least one location is received from, for example, a user device (e.g., the user device 110). In an embodiment, the at least one location may be received as coordinates such as, for example, an address, a global positioning system (GPS) signal, and the like. The coordinates may be static (e.g., a certain address) or dynamic (e.g., a certain route through which the user device 110 passes).

In S220, at least one time parameter is received. In an embodiment, each time parameter may be a certain time period such as, for example, the month of January 2016. In S230, at least one air pollution source within a predetermined perimeter based on the at least one location are identified.

In S240, an air quality score range is extracted based on the perimeter. In S250, at least one environmental variable is identified based on the perimeter. In S260, at least one air pollution measurement is simulated based on the environmental variables. In S270, at least one air quality score respective of the air quality score range is generated based on the at least one air pollution measurement. In S280, it is checked whether additional locations and/or time parameters have been received and, if so, execution continues with S210; otherwise, execution terminates.

Figure 3:
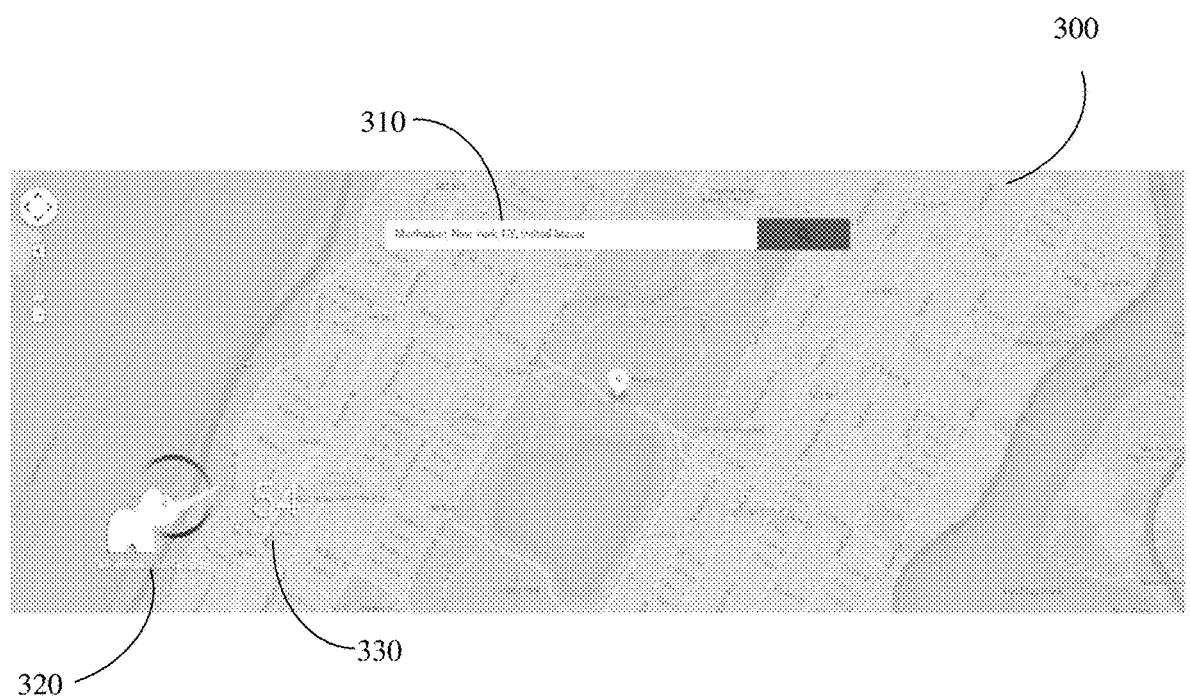
FIG. 3 is a simulation of an air quality map of air quality scores according to an embodiment.

FIG. 3 is an exemplary and non-limiting simulation of an air quality map 300 according to an embodiment. The air quality map includes a search bar 310 through which a user via, for example, a user device (e.g., the user device 110) can input a certain location. The location is analyzed and an air quality score 320 is generated as further described hereinabove. In this exemplary simulation, the air quality score is 54. The air quality score 320 is then displayed on the air quality map 310. In a further embodiment, an air pollution measurement is further displayed 330 on the air quality map 310.

The various embodiments may be implemented as hardware, firmware, software, or any combination thereof. Moreover, the software is preferably implemented as an application program tangibly embodied on a program storage unit or tangible computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such computer or processor is explicitly shown. In addition, various other peripheral units may be connected to the computer platform such as an additional data storage unit and a printing unit. All or some of the servers maybe combined into one or more integrated servers. Furthermore, a non-transitory computer readable medium is any computer readable medium except for a transitory propagating signal. The display segments and mini-display segments may be shown on a display area that can be a browser or another other appropriate graphical user interface of an internet mobile application, either generic or tailored for the purposes described in detail hereinabove.

All examples and conditional language recited herein are intended for pedagogical purposes to aid the reader in understanding the principles and the concepts contributed by the inventor to furthering the art, and are to be construed as being without limitation to such specifically recited examples and conditions. Moreover, all statements herein reciting principles, aspects, and embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. A computerized method for generating air quality scores based on at least one location, a predetermined perimeter, and at least one time parameter, comprising:

identifying, by a server, at least one air pollution source within the predetermined perimeter around the at least one location, wherein the predetermined perimeter is a predetermined geometric shape defined geometrically with respect to the at least one location, wherein said identifying comprises querying a data source to obtain the at least one air pollution source that is located within the predetermined perimeter around the at least one location, wherein the at least one air pollution source is a source emitting air pollution that is selected from the group consisting of: heavy transportation, generating stations, factories, and incineration of garbage;

extracting, by the server, an air quality score range based on the at least one location from at least one data source;

identifying, by the server, at least one environmental variable based on the at least one location and the at least one time parameter, wherein said identifying the at least one environment variable comprises extracting the at least one environmental variable an external server, wherein the at least one environmental variable is any of: meteorological parameters, topographic parameters, and traffic parameters;

simulating, by the server, at least one air pollution measurement for the at least one location, wherein said simulating is performed based on the at least one environmental variable and the at least one air pollution source, wherein said simulating is further based on historical environmental variables associated with the at least one air pollution source, whereby automatically estimating an air pollution measurement for the at least one location using data available about the at least one air pollution source; and generating, by the server, at least one air quality score respective of the air quality score range, wherein the at least one air quality score is based on the at least one air pollution measurement.

2. The computerized method of claim 1, further comprising:

generating at least one recommendation based on the at least one air quality score.

3. The computerized method of claim 2, wherein the at least one recommendation is generated based on a type of the at least one air pollution source.

4. The computerized method of claim 2, further comprising:

generating at least one personalized recommendation based on at least one personal variable related to a user.

5. The computerized method of claim 2, wherein said generating the at least one recommendation comprises: determining a route from a first location to a second location having a minimal air pollution exposure, wherein said determining the route is based on the at least one air quality score.

6. The computerized method of claim 1, wherein the at least one location or the at least one time parameter is received from a user device, wherein the user device is coupled via a network to the server.

7. The computerized method of claim 1, further comprising:
generating an air pollution score respective of the at least one air pollution source based on the at least one air quality score.

8. The computerized method of claim 1, wherein the meteorological parameters are any of: wind speed, wind direction, air temperature, air pressure, air humidity, precipitation, haze, contents of the air, solar radiation, and terrestrial radiation.

9. The computerized method of claim 1, further comprising:
generating an air quality map based on the at least one air quality score; and
displaying the air quality map.

10. The computerized method of claim 1, further comprising:
generating future air quality scores based on the at least one air quality score.

11. The computerized method of claim 1, wherein predetermined geometric shape defined geometrically with respect to the at least one location is a predetermined geometric shape selected from the group consisting of a circular area, a triangular area, and a square area.

12. The computerized method of claim 1, wherein predetermined geometric shape defined geometrically with respect to the at least one location is a geometric shape having the at least one location at a geometric center thereof.

13. A system for generating air quality score based on at least one location, a predetermined perimeter, and at least one time parameter, comprising:
a processor; and
a memory, the memory containing instructions that, when executed by the processor, configure the system to:
identify at least one air pollution source within the predetermined perimeter around the at least one location, wherein the predetermined perimeter is a predetermined geometric shape defined geometrically with respect to the at least one location, wherein the system is configured to identify the at least one air pollution source by querying a data source to obtain the at least one air pollution source that is located within the predetermined perimeter around the at least one location, wherein the at least one air pollution source is a source emitting air pollution that is selected from the group consisting of: heavy transportation, generating stations, factories, and incineration of garbage;
extract an air quality score range based on the at least one location from at least one data source;
identify at least one environmental variable based on the at least one location and the at least one time parameter, wherein the system is configured to identify the at least one environment variable by extracting the at least one environmental variable an external server, wherein the at least one environmental variable is any of: meteorological parameters, topographic parameters, and traffic parameters;
simulate at least one air pollution measurement for the at least one location, wherein said simulating is performed based on the at least one environmental variable and the at least one air pollution source, wherein said simulating is further based on historical environmental variables associated with the at least one air pollution source, whereby automatically estimating an air pollution measurement for the at least one location using data available about the at least one air pollution source; and
generate at least one air quality score respective of the air quality score range, wherein the at least one air quality score is based on the at least one air pollution measurement.

14. The system of claim 13, wherein the system is further configured to:
generate at least one recommendation based on the at least one air quality score.

15. The system of claim 14, wherein the at least one recommendation is generated based on a type of the at least one air pollution source.

16. The system of claim 14, wherein the system is configured to generate the at least one recommendation by determining a route from a first location to a second location having a minimal air pollution exposure, wherein said determining the route is based on the at least one air quality score.

17. The system of claim 13, wherein the at least one location or the at least one time parameter is received from a user device, wherein the user device is coupled via a network to the system.

18. The system of claim 13, wherein the system is further configured to:
generate at least one personalized recommendation based on at least one personal variable related to a user.

19. The system of claim 13, wherein the system is further configured to:
generate an air pollution score respective of the at least one air pollution source based on the at least one air quality score.

20. The system of claim 13, wherein the meteorological parameters include any of: wind speed and direction, air temperature, air pressure, air humidity, precipitation, haze, contents of the air, solar radiation, and terrestrial radiation.

21. The system of claim 13, wherein the system is further configured to:
generate an air quality map based on the at least one air quality score; and
display the air quality map.

22. The system of claim 13, wherein the system is further configured to:
generate future air quality scores based on the at least one air quality score.

23. A computerized method for generating air quality scores based on a first location, a second location, and a predetermined geometric shape, comprising:
identifying, by a server, a first air pollution source within a first perimeter that is defined geometrically using the predetermined geometric shape with respect to the first location, wherein said identifying comprises querying a data source to obtain the first air pollution source that is located within the first perimeter around the first location, wherein the first air pollution source is a source emitting air pollution that is selected from the group consisting of: heavy transportation, generating stations, factories, and incineration of garbage;
extracting, by the server, a first air quality score range based on the first location from at least one data source;
identifying, by the server, a first environmental variable based on the first location and a first time parameter, wherein said identifying the first environment variable comprises extracting the first environmental variable from an external server, wherein the first environmental variable is selected from the group consisting of: meteorological parameters, topographic parameters, and traffic parameters;

simulating, by the server, a first air pollution measurement for the first location, wherein said simulating is performed based on the first environmental variable and the first air pollution source, wherein said simulating is further based on historical environmental variables associated with the first air pollution source, whereby automatically estimating a first air pollution measurement for the first location using data available about the first air pollution source;

generating, by the server, a first air quality score respective of the first air quality score range, wherein the first air quality score is based on the first air pollution measurement;

identifying, by the server, a second air pollution source within a second perimeter that is defined geometrically using the predetermined geometric shape with respect to the second location, wherein said identifying comprises querying a data source to obtain the second air pollution source that is located within the second perimeter around the second location, wherein the second air pollution source is a source emitting air pollution that is selected from the group consisting of: heavy transportation, generating stations, factories, and incineration of garbage;

extracting, by the server, a second air quality score range based on the second location from at least one data source;

identifying, by the server, a second environmental variable based on the second location and a second time parameter, wherein said identifying the second environment variable comprises extracting the second environmental variable from an external server, wherein the second environmental variable is selected from the group consisting of: meteorological parameters, topographic parameters, and traffic parameters;

simulating, by the server, a second air pollution measurement for the second location, wherein said simulating is performed based on the second environmental variable and the second air pollution source, wherein said simulating is further based on historical environmental variables associated with the second air pollution source, whereby automatically estimating a second air pollution measurement for the second location using data available about the second air pollution source; and generating, by the server, a second air quality score respective of the second air quality score range, wherein the second air quality score is based on the second air pollution measurement.

* * * * *